United States Patent [19]

Forsyth et al.

[11] Patent Number: 5,114,544
[45] Date of Patent: May 19, 1992

[54] PRODUCTION OF FLUOROCARBONS

[75] Inventors: Steven R. Forsyth, Chester; Brian T. Grady, Cheshire, both of England

[73] Assignee: Imperial Chemical Industries PLC, London, England

[21] Appl. No.: 644,741

[22] Filed: Jan. 23, 1991

Related U.S. Application Data

[63] Continuation of Ser. No. 412,313, Sep. 26, 1989, abandoned.

[30] Foreign Application Priority Data

Sep. 26, 1988 [GB] United Kingdom ............. 8822541

[51] Int. Cl.$^5$ ..................... G25B 3/04; C07C 19/08
[52] U.S. Cl. ............................. 204/59 F; 204/130; 570/134; 570/176
[58] Field of Search .............. 204/130, 140, 59 R, 204/59 F; 570/134, 135, 136, 155, 176

[56] References Cited

U.S. PATENT DOCUMENTS

| | | | |
|---|---|---|---|
| 3,391,204 | 7/1968 | Young | 570/156 |
| 3,884,776 | 5/1975 | Keidel | 204/73 R |
| 4,334,105 | 6/1982 | Terrell et al. | 568/683 |
| 4,365,097 | 12/1982 | Terrell et al. | 568/684 |
| 4,409,076 | 10/1983 | Seidel et al. | 204/130 |

FOREIGN PATENT DOCUMENTS 997315 7/1965 United Kingdom .
1017815 1/1966 United Kingdom .

OTHER PUBLICATIONS

McGraw-Hill Encyclopedia of Science & Technology, 6th ed., vol. 3, pp. 284-285 and vol. 8, pp. 498-500, New York.

Primary Examiner—John Niebling
Assistant Examiner—Steven P. Marquis
Attorney, Agent, or Firm—Cushman, Darby & Cushman

[57] ABSTRACT

A process for the production of a fluorocarbon by reducing a fluorocarbon which contains at least one atom of chlorine and/a bromine, in which the reduction is effected in the presence of a redox couple. The redox couple, which is oxidized in the process, may be reduced electrolytically for re-use in the process. A preferred redox couple is a chromous-chromic couple.

17 Claims, No Drawings

PRODUCTION OF FLUOROCARBONS

This is a continuation of application Ser. No. 412,313, filed on Sep. 26, 1989, which was abandoned upon the filing hereof.

This invention relates to a process for the production of fluorocarbons and in particular to the production of fluorohydrocarbons by reduction of fluorocarbons containing chlorine and/or bromine.

Chlorofluorocarbons, otherwise known as CFC's, are used on a large scale throughout the world, for example, as refrigerants and lubricants, but particularly as propellants for aerosol sprays in which the variety of applications is virtually unlimited. In some of the applications of CFC's the CFC's are released into the atmosphere. Release of CFC's into the atmosphere may occur, for example, through leakages in refrigeration systems or when refrigeration systems are dismantled, and large quantities are also released through aerosal applications of CFC's. In recent years the presence of CFC's in the upper atmosphere has been postulated as a cause of the partial destruction of the ozone layer in the upper atmosphere which has recently been detected. Even a partial destruction of this ozone layer may have the effect of producing an increase in temperature over the surface of the earth with potentially disastrous effects, that is the so-called "greenhouse effect".

In view of this perceived adverse effect of CFC's on the ozone layer and hence on the temperature over the surface of the earth attempts have been made to find suitable replacements for CFC's which will perform at least adequately in the many applications in which CFC's are used but which will not have a damaging effect on the ozone layer, or at least will not have such a damaging effect as it is believed do the CFC's currently used. The search for suitable replacements for CFC's has in general centred on fluorocarbons which contain hydrogen and which can in principle be produced inter alia by reduction of CFC's by a process in which one or more chlorine atoms in the CFC molecule are replaced by hydrogen. An example of a possible replacement for CFC's currently in use is the fluorohydrocarbon having the formula $CF_3-CFH_2$.

Processes have already been described for the reduction of fluorocarbons containing chlorine and/or bromine, particularly electrochemical processes. By way of example of prior descriptions of such processes there may be mentioned Italian patent 852487 which describes a process for the production of unsaturated chlorofluoro- or fluorocarbons and/or saturated chlorofluoro or fluorohydrocarbons by electrolytic reduction of saturated chlorofluorocarbons having the same number of carbon atoms. In the process the saturated chlorofluorocarbon is dissolved in a solvent which also contains an electrolyte and the electrolytic reduction is effected in an electrolytic cell consisting of two electrodes. The electrolytic cell may be undivided or it may comprise a porous separator. The cathode in the electrolytic cell is mercury, indeed mercury is the only material specifically described as being suitable for use as a cathode. The use of mercury as a cathode at which to effect the reduction is not surprising as mercury has the highest overpotential known for the electrolytic production of hydrogen. USSR Patent 230 131 describes a process for the preparation of fluorolefines by dehalogenation of "Freons" in which, with the aim of increasing the yield of the desired product and improving its purity, the dehalogenation of the "Freons" is performed electrochemically in an electrolytic cell in neutral or alkaline medium in the presence of an organic solvent with the addition to the catholyte of soluble compounds of metals, for example lead. In the process the favoured material for use as the cathode in the electrolytic cell is lead. USSR Patent 702 702 describes a process for the production of 1,1,2-trifluorochloroethylene by electrochemical dechlorination of 1,1,2-trifluorotrichloroethane in the presence of an electrolyte which is a soluble salt of a metal in neutral or weakly alkaline medium using a metallic cathode in which, with the aim of improving the yield of the desired product, simplifying, intensifying and rendering the process continuous, a porous hydrophobised metal is used as the metallic cathode, the starting 1,1,2-trifluorotrichloroethane being supplied to the cathode from its reverse side.

Although such electrochemical reduction processes may be used to reduce fluorocarbons containing chlorine and/or bromine we have found that such processes suffer from a disadvantage in that it sometimes is not possible to reduce some fluorocarbons, possibly because the required reduction potential is too high, in which case the electrochemical process results in production of hydrogen rather than in the desired reduction of the fluorocarbon.

The present invention relates to a process which in many cases may be operated to overcome the aforementioned disadvantage and which may be used to reduce fluorocarbons containing chlorine and/or bromine which in some cases cannot be reduced by electrochemical processes.

The present invention provides a process for the production of a fluorocarbon by reducing a fluorocarbon which contains at least one atom of chlorine and/or bromine, in which the reduction is effected in the presence of a redox couple.

In the process of the invention the redox couple, is oxidized from a lower valency reduced state to a higher valency oxidized state, and in a preferred embodiment of the process the redox couple which has been oxidized is itself reduced electrolytically back to a reduced state suitable for re-use in the process of the invention. This preferred embodiment thus provides a multi-step cyclic process for the production of a fluorocarbon by reducing a fluorocarbon which contains at least one atom of chlorine and/or bromine, in which the reduction is effected in the presence of a redox couple, which in the process is oxidized, the reduced fluorocarbon is separated, and the oxidized redox couple is reduced electrolytically to a reduced state and is re-used in the fluorocarbon reduction step of the process. The reduction may be effected in a solution of the redox couple, which may be a solution in a protic or aprotic solvent, and the reduced fluorocarbon may be separated from the solvent.

We are aware that redox couples have previously been described as reagents suitable for effecting dehalogenation reactions. For example, in the Journal of the American Chemical Society 88 4094 (1966) there is described a process in which an alkyl halide is reduced in the presence of a chromous salt, in the Journal of Organic Chemistry 33 1027 (1968) there is described the reductive cyclization of α-ω-dihalides in the presence of chromous complexes, and in the Canadian Journal of Chemistry 55 2420 (1977) there is described the reductive elimination of halogen from haloalkanes in the presence of chromous, cuprous and stannous ions. We are not aware of any prior disclosure of the use of a redox couple to reduce a fluorocarbon containing chlorine and/or bromine, nor are we aware of any prior suggestion of the use of a redox couple to selectively remove chlorine and/or bromine from a fluorocarbon containing at least one atom of chlorine and/or bromine. The process of the present invention provides a particularly convenient way of effecting such a selective removal of chlorine and/or bromine.

The fluorocarbon which is reduced in the process of the invention comprises at least one atom of chlorine and/or bromine, and in general the fluorocarbon which is reduced will be saturated. The fluorocarbon which is reduced may have the formula R-X in which R represents an alkyl group having at least one fluorine atom and X represents chlorine and/or bromine. The fluorocarbon which is reduced in the process of the invention may comprise more than one atom of chlorine and/or bromine, and in the fluorocarbon of formula R-X the group R may contain one or more atoms of chlorine and/or bromine.

The fluorocarbon may be reduced in the process to a saturated fluorohydrocarbon or to an unsaturated fluorocarbon. Thus, fluorocarbon R-X may be reduced in the process to a saturated fluorohydrocarbon R-H, or it may be reduced to an unsaturated fluorocarbon. Whether or not a saturated fluorohydrocarbon or an unsaturated fluorocarbon is produced in the reduction process depends to some extent on the structure of the fluorocarbon which is reduced. For example, where the alkyl group R in the fluorocarbon R-X itself contains one or more chlorine and/or bromine atoms, and where the group R contains two or more carbon atoms and the chlorine and/or bromine atoms which are present in the fluorocarbon R-X are present on the same carbon atom, the production of a saturated fluorohydrocarbon R-H may be favoured, depending on certain other factors which will be referred to hereafter. On the other hand, where the group R contains two or more carbon atoms and one or more chlorine and/or bromine atoms, and the chlorine and/or bromine atoms in the fluorocarbon R-X are present on adjacent carbon atoms, the production of an unsaturated fluorocarbon by reductive dehalogenation may be favoured, depending once again on certain other factors which will be referred to hereafter.

The following examples of fluorocarbon reductions which may be effected in the process of the invention are merely by way of example and are not intended to be in any way limiting. Thus, fluorocarbons containing chlorine and/or bromine which may be reduced in the process of the invention include substituted methanes, for example bromofluoromethane and substituted ethanes, for example 1,1,2-trichloro-1,2,2-trifluoroethane and compounds of the formula $$CF_3CClYZ$$

wherein each of Y and Z, independently, represents hydrogen, chlorine or fluorine. Merely by way of example a fluorocarbon having the formula $CF_3$—$CFCl_2$ may be reduced to the saturated fluorohydrocarbon $CF_3$—$CFClH$ and to $CF_3CFH_2$. On the other hand the isomeric fluorocarbon $CF_2Cl$—$CF_2Cl$ may be reduced by way of reductive dechlorination to yield the unsaturated fluorocarbon $CF_2$=$CF_2$, that is tetrafluoroethylene. The fluorocarbon which is to be reduced in the process of the invention may be a substantially pure compound or it may be in the form of a mixture, particularly a mixture of isomers. For example, where the fluorocarbon which is to be reduced is $CF_3$—$CFCl_2$ it may be the substantially pure compound or it may be used in the form of a commercially available mixture with the isomer $CF_2Cl$—$CF_2Cl$. Using such a mixture of isomers it is possible to convert the compound $CF_3CFCl_2$ to $CF_3CFClH$ in very high yield whilst leaving the compound $CF_2Cl$—$CF_2Cl$ virtually unchanged or at most converting a small amount to $CF_2$=$CF_2$. Suitable mixtures contain at least 1%, and typically from 5 to 95%, of the compound $CF_3CFCl_2$ on a weight basis. The method of the invention thus provides a convenient method for increasing the content of $CF_2Cl$—$CF_2Cl$ in a mixture of the isomers.

The redox couple comprises a compound of a metal which exists in a plurality of oxidation states, the reduction in the process of the invention being effected by the metal or a compound of the metal in a lower oxidation state and in the process the metal or compound thereof being oxidized to a higher oxidation state. The metal of the compound in the redox couple has a negative redox potential and it is preferred that the redox potential be at least $-0.15$ volts, that is at least 0.15 volts or more negative. Metals which exist in a plurality of oxidation states and which are suitable for use in the redox couple, and the redox potentials of the metals, are as follows $$Ti^{3+} + e^- \rightarrow Ti^{2+} \quad -0.37 \text{ v}$$

$$V^{3+} + e^- \rightarrow V^{2+} \quad -0.26 \text{ v}$$

$$Cr^{3+} + e^- \rightarrow Cr^{2+} \quad -0.41 \text{ v}$$

$$Zn^{2+} + 2e^- \rightarrow Zn^0 \quad -0.76 \text{ v}$$

However, this list is not intended to be limiting and is given merely by way of example, and other redox couples may be used in the process of the invention. Any suitable compound of the metal may be used in the redox couple but it is preferred that the compound is soluble, e.g. in the solvent, if any, in which the process of the invention is effected, and it is more preferred that the compound of the metal in both its lower and higher oxidation sates is soluble. Solubility aids smooth operation of the process. Thus, the choice of compounds of the metal in the redox couple will be dictated at least to some extent by the nature of the solvent which is used in the process and on whether or not the solvent is a protic solvent or an aprotic solvent. The salt may be a salt of a strong acid or of a weak acid. For example, the salt may be a halide, e.g. a chloride or bromide, or it may be a nitrate or sulphate. The salt may be a salt of an organic acid, e.g. an acetate or a propionate.

A preferred redox couple is the chromous-chromic couple as it is particularly effective when used in the reduction of fluorocarbons.

It is to be understood that not all fluorocarbons containing at least one atom of chlorine and/or bromine may be reduced by all redox couples, nor that all fluorocarbons containing at least one atom of chlorine and/or bromine may be reduced to the desired extent. It is because the chromous-chromic couple is particularly effective as a reducing agent for a variety of different such fluorocarbons that this redox couple is preferred. The effectiveness of the redox couple in effecting reduction may also be increased by carrying out the process in the presence of a complexing agent for the metal in the redox couple. Example of such complexing agents include polyamines, e.g. aklylene diamines, for example ethylene diamines. Another complexing agent is ethylene diamine tetraacetic acid.

The fluorocarbon containing at least one atom chlorine and/or bromine is suitably subjected to reduction in a liquid solvent in which the fluorocarbon is at least dispersible but in which it is preferably soluble. The solvent may be aprotic, that is not having labile hydrogen, and use of such a solvent favours the production of an unsaturated fluorocarbon rather than a saturated fluorohydrocarbon. Examples of aprotic solvents include acetonitrile, dichloromethane, dimethyl formamide, carbon tetrachloride, propylene carbonate, dimethyl sulphoxide, tetrahydrofuran and dioxane. On the other hand, the solvent may be a protic solvent having labile hydrogen, and use of such a solvent favours the production of a saturated fluorohydrocarbon rather than an unsaturated fluorocarbon. Examples of protic solvents include water, alcohols, e.g. methanol and, ethanol, phenols, and carboxylic acids, e.g. acetic acid. Particularly preferred are aqueous solutions, for example aqueous solutions of alcohols, e.g. of methanol, especially where production of a saturated fluorohydrocarbon is desired.

Use of a low boiling point solvent may be favoured as such a solvent may easily be separated from the redox couple, e.g. by evaporation, prior to regeneration of the redox couple.

Where the redox couple is to be regenerated electrolytically for re-use in the process of the invention the solvent may comprise an electrolyte dissolved therein. Examples of suitable electrolytes include halides and hydroxides of alkali metals, e.g. sodium hydroxide and potassium hydroxide. Suitable concentrations of electrolyte may depend on the nature of the solvent. For example, where the solvent is an aprotic solvent the concentration of the electrolyte is suitably in the range 0.1 to 0.5M, whereas where the solvent is a protic solvent the concentration of electrolyte is suitably in the range of 0.1 to 3M, although these concentrations ranges are meant to be for guidance only. However, the redox couple itself may also serve as the electrolyte in the electrolytic regeneration step.

The concentration of the fluorocarbon which is reduced in the process of the invention may vary over a wide range, e.g. over a range of from 10% to 60% weight/volume.

The concentration of the redox couple may vary over a wide range. e.g. it may be in the range of, for example $10^{-3}$M to 3M.

The conditions under which the reduction process of the invention is effected may also vary over a broad range.

The temperature at which the reduction process is effected will be governed by the nature of the fluorocarbon containing chlorine and/or bromine, and the nature of the saturated or unsaturated fluorocarbon which is produced in the process. As these fluorocarbons are generally gaseous at normal temperature the process may be operated at elevated pressure, e.g. at a pressure of up to 5 bar or even 10 bar or more, depending on the design of the reaction vessel, and in general a temperature of between $-15°$ C. and $50°$ C., or even $80°$ C., may be used. The rate at which the reduction process proceeds may also be governed by the temperature and where increased rates of reduction are desired an elevated temperature is preferred.

The progress of the reduction process may be monitored by conventional analytical procedures, particularly by gas - liquid chromatography When reduction of the fluorocarbon containing at least one atom of chlorine and/or bromine has been effected in the process of the invention the reduced fluorocarbon may be separated, for example from the solvent which may have been used. As many of the fluorocarbons are gaseous at normal temperature and as the reduction process will generally be effected under pressure the reduced fluorocarbon may be separated by allowing it to evaporate.

The reduced fluorocarbon may be subjected to distillation in order to purify the reduced fluorocarbon and to separate it from any unreduced fluorocarbon and from reduced fluorocarbon products which are not desired.

Regeneration of the redox couple, that is reduction of the metal of the redox couple from a higher valency oxidized state to a lower valency reduced state may be effected electrolytically. The conditions used in effecting the reduction will depend on the nature of the redox couple, but suitable conditions will readily be selected by the man skilled in the art.

Reduction may be effected in an electrolytic cell, which may be an undivided cell. Alternatively, reduction may be effected in a divided cell equipped with, for example, an ion-exchange membrane in which case reduction will be effected in the cathode compartment of the cell. The electrolytic cell in which the reduction is effected may be equipped with metallic electrodes.

The invention is illustrated by the following examples.

EXAMPLE 1

2 m moles of chromous chloride and 3 m moles of the disodium salt of ethylene diamine tetraacetic acid in 10 ml of a 90% by weight solution of dimethyl formamide in water were charged to a reaction vessel and the vessel was sealed.

The vessel was heated to $60°$ C. and 2 ml of $CF_3CFHCl$ in gaseous form were injected into the vessel and the vessel and contents were agitated at the temperature of $60°$ C. for 10 minutes.

After 10 minutes a sample of the gas in the space above the liquid in the reaction vessel was withdrawn from the vessel and analysed by gas-liquid chomatography. Analysis indicated that 50% of the $CF_3CFHCl$ has been reduced and that of the reduced product 94% was in the form of $CF_3CFH_2$.

EXAMPLE 2

The procedure of Example 1 was repeated except that 10 ml of $CF_3CFHCl$ in gaseous form was injected into the reaction vessel to which 5 m moles of chromous chloride and 24 m moles of n-butylamine in 4 ml of water had previously been charged, and the reaction vessel and contents were agitated for 20 minutes at a temperature of $80°$ C. Analysis of the gas space above the liquid in the reaction vessel showed that virtually 100% of the $CF_3CFHCl$ had been reduced and that the yield of $CF_3CFH_2$ was 77% and the yield of $CF_2=CFH$ was 23%.

EXAMPLE 3

The procedure of Example 1 was repeated except that 2.5 g of chromous chloride and 10 ml of dimethylformamide containing 30 m moles of ethylene diamine were charged to the reaction vessel, and, when the chromous chloride had dissolved, 0.1 ml of $CF_3CFHCl$ in liquid form was injected into the reaction vessel. The reaction vessel and contents were agitated for 2 hours at 20° C. Analysis of the gas space above the liquid in the reaction vessel indicated that the $CF_3CFHCl$ had been completely reduced and that the yield of $CF_3CFH_2$ was 57% and the yield of $CF_2=CFH$ was 43%.

EXAMPLE 4

The procedure of Example 1 was repeated except that 10 ml of dimethylformamide and 0.5 g of chromous chloride were charged to the reaction vessel and thereafter 0.2 ml of gaseous $CF_2ClCF_2Cl$ was injected into the reaction vessel. The vessel and contents were agitated for 2 hours at 20° C. and analysis indicated that $CF_2=CF_2$ was produced in 98% yield.

EXAMPLE 5

The procedure of Example 1 was repeated except that 10 ml of an 80% by weight solution of dimethylformamide in water and 1 g of chromous chloride were charged to the reaction vessel and thereafter 0.1 ml of $CF_2Cl\ CFCl_2$ in liquid form was injected into the vessel. The vessel and contents were agitated for 12 hours at 20° C. and analysis indicated that $CF_2=CFH$ had been produced.

EXAMPLE 6

Regeneration of redox couple. 24 g of chromic chloride $CrCl_3$ was dissolved in 30 ml of water and used as the catholyte in an electrolyte cell. The separator in the cell was a "Nafion" perfluorosulphonic type cation exchange membrane and 30% w/w aqueous sulphuric acid was used as the anolyte. The anode was a 6 cm² platinum sheet and the cathode was a pool of mercury of 11 cm² area. The catholyte was thoroughly degassed with nitrogen prior to, and during, electrolysis. A constant current of 1.13 A was discharged through the cell for 150 minutes. The catholyte changed from dark green in colour to deep sky blue of $CrCl_2$ and was suitable for use as a redox couple.

EXAMPLE 7

The procedure of Example 1 was repeated except that 1 ml of a 3M dm$^{-3}$ aqueous chromous chloride solution and 9 ml of a dimethylformamide solution containing 0.5 m moles of $CF_3CCl_3$ were charged to the reaction vessel. After 11 hours at 20° C. analysis indicated that the yield of $CF_3CH_2Cl$ was 60% and the yield of $CF_2=CH_2$ was 28%.

EXAMPLE 8

The procedure of example 7 was repeated except 0.5 m moles of $CF_2Cl-CFHCl$ was used. Analysis indicated that the yield of $CF_2=CFH$ was 95% and that 56% of the $CF_2Cl-CFHCl$ had reacted.

EXAMPLE 9

The procedure of example 7 was repeated except 0.5 m moles of $CH_3-CHCl_2$ was used. Analysis indicated that the yield of $CF_3CH_2Cl$ was 84% and the yield of $CF_2=CH_2$ was 15%.

EXAMPLE 10

The procedure of example 6 was repeated except 0.5 mmoles of $CF_2Cl-CHCl_2$ was used. Analysis indicated that the yield of $CF_2=CHCl$ was 98%.

EXAMPLE 11

1.1 mmoles of ethylenediamine tetraacetic acid were added to 1 ml of a 1.1M dm$^{-3}$ aqueous chromous chloride solution and the resultant solution was added to a reaction vessel as used in example 1 containing 0.2 mmoles of $CF_2Cl-CH_3$ is 9 ml of Dimethyl foramide. The reaction vessel was sealed and after 11 hours at 80° C., analysis showed that 56% of the $CF_2Cl-CH_3$ had been reduced.

EXAMPLE 12

1 ml of a 1.1M dm$^{-3}$ aqueous chromous chloride solution was added to 9 ml of a dimethylformamide solution containing 0.2 mmoles of $CF_3CHClBr$ in a reaction vessel following the procedure of Example 11. After 11 hours at 20° C. analysis showed that the yield of $CF_3CH_2Cl$ was 56% and the yield of $CF_2=CH_2$ was 43%.

EXAMPLE 13

The procedure of example 6 was repeated except tetrahydrofuran was used instead of dimethylformamide. Analysis indicated that the yield of $CF_3CH_2Cl$ was 42%, the yield of $CF_3CHCl$, was 23% and the yield of $CF_2=CH_2$ was 31%.

We claim:
1. In a process for the production of a fluorocarbon by reducing a fluorocarbon which contains at least one atom selected from the group consisting of chlorine and bromine in the presence of a reducing agent, wherein the resulting reduction, the atom of chlorine and/or bromine is replaced by hydrogen said process comprising steps wherein the reduction is effected in the presence of a solution of a reducing agent which reducing agent consists essentially of a redox couple which comprises a metal or a compound of a metal which exists in a plurality of states, the reduction being effected by the metal or compound of the metal in a lower oxidation state and being oxidized to a higher oxidation state in the process reducing the oxidized redox couple electrolytically and reusing the redox couple in the fluorocarbon reduction step of the process.

2. A process as claimed in claim 1 in which the fluorocarbon which is reduced in the process is a saturated fluorocarbon.

3. A process as claimed in claim 1 in which the fluorocarbon which is reduced in the process has the formula R-X in which R represents an alkyl group having at least one fluorine atom and X is selected from the group consisting of chlorine and bromine.

4. A process as claimed in claim 1 in which the fluorocarbon which process to a saturated fluorocarbon.

5. A process as claimed in claim 4 in which a fluorocarbon R-X is reduced to a fluorohydrocarbon R-H.

6. A process as claimed in claim 1 in which the fluorocarbon which is reduced in the process has the formula

$CF_3\ CCl\ YZ$ where each of Y and Z represents hydrogen chlorine, or fluorine.

7. A process as claimed in claim 6 in which $CF_3CFCl_2$ is reduced to at least one member of the group consisting of $CF_3CFClH$ and $CF_3\ CFH_2$.

8. A process as claimed in claim 1 in which the redox couple comprises a compound of a metal which exists in a plurality of oxidation states.

9. A process as claimed in claim 1 in which the redox potential is at least −0.15 volts.

10. A process as claimed in claim 1 in which the redox couple is a chromous-chromic couple.

11. A process as claimed in claim 1 which is effected in a protic or in an aprotic solvent.

12. A process as claimed in claim 14 which is effected in an aqueous solution.

13. A process as claimed in claim 1 in which the concentration of fluorocarbon which is reduced is in the range 10% to 60% weight of volume.

14. A process as claimed in claim 1 in which the concentration of the redox couple is in the range $10^{-3}$M to 3M.

15. A process according to claim 1 wherein the metal in the redox couple has a negative redox potential of at least −0.15 volts.

16. A multi-step process for the production of a fluorocarbon by reducing a fluorocarbon which contains at least one atom selected from the group consisting of chlorine and bromine in the presence of a reducing agent, wherein the resulting reduction, the atom of chlorine and/or bromine is replaced by hydrogen, wherein the reduction is effected in the presence of a solution of a reducing agent which reducing agent consists essentially of a redox couple which comprises a metal or compound of a metal which exists in a plurality of states, the reduction being effected by the metal or compound of the metal in a lower oxidation state and being oxidized to a higher oxidation state in the process, separating the reduced fluorocarbon, reducing the oxidized redox couple electrolytically and reusing the redox couple in the fluorocarbon reduction step of the process.

17. A process as claimed in claim 16 in which the reduction is effected in the presence of a solution of the redox couple.

* * * * *